United States Patent [19]

Niwa et al.

[11] Patent Number: 5,618,734

[45] Date of Patent: Apr. 8, 1997

[54] METHOD FOR MEASURING 3-DEOXYGLUCOSONE DERIVATIVES IN A SAMPLE

[75] Inventors: Toshimitsu Niwa, Kounan; Koichi Niimura, Warabi; Minoru Ohara, Tokyo; Sigemi Tomiyama, Matsudo, all of Japan

[73] Assignee: Kureha Chemical Industry Co., Ltd., Tokyo, Japan

[21] Appl. No.: 406,704

[22] Filed: Mar. 20, 1995

Related U.S. Application Data

[62] Division of Ser. No. 314,687, Sep. 29, 1994.

[30] Foreign Application Priority Data

Sep. 29, 1993 [JP] Japan ................................. 5-264092

[51] Int. Cl.$^6$ ........................ G01N 30/06; G01N 30/14; G01N 30/72
[52] U.S. Cl. .................... 436/173; 436/8; 436/14; 436/56; 436/94; 436/95; 436/128; 436/161; 436/174; 436/177; 436/57
[58] Field of Search ................................. 436/8, 14, 56, 436/94, 95, 128, 161, 173, 174, 177

[56] References Cited

U.S. PATENT DOCUMENTS

| 4,224,031 | 9/1980 | Mee et al. ............................. 436/173 |
| 4,709,016 | 11/1987 | Giese . |
| 5,302,758 | 4/1994 | Larson et al. .......................... 436/173 |

FOREIGN PATENT DOCUMENTS 4-145360  5/1992  Japan .

OTHER PUBLICATIONS

H. El Khadem et al., "New Route for the Synthesis of 3–Deoxyaldos–2–ulose," *Carbohydrate Research*, vol. 17, 183–192 (1971).
T. Shinoda et al., "Physiological Activity and Metabolism of 3–Deoxyglucosone," *the Maillard Reaction in Food Processing, Human Nutrition and Physiology*, 309–314 (1990).
*Chemical Abstracts* 1986:605466, L. Den Drijver et al., *J. Chromatog.*, 363:345–352 (1986).
"Detection of 3–Deoxyfructose and 3–Deoxyglucosone in Human Urine and Plasma; Evidence of Intermediate Stages of Maillard Reaction in Vivo[1]", Knecht et al., Archives of Biochemistry and Biophysics, vol. 294, No. 1, Apr., pp. 130–137, 1992.
"Chemical Abstracts", C. Paul Blanchi, vol. 113, No. 13, p. 89, 1990.
B.L. Wedzicha et al. *Food Chem.* 1991, 39, 73–86.
H. Kato et al. *Biochim. Biophys. Acta* 1990, 1035, 71–76.
T.P. Mawhinney et al. *Anal. Biochem.* 1980, 101, 112–117.
E.E. Kingston et al. *Biomed. Mass Spectrom.* 1978, 5, 621–626.
E. White et al. *Biomed. Mass Spectrom.* 1982, 9, 395–405.
J.A. Jonckheee et al. *Biomed. Mass Spectrom.* 1983, 10, 197–202.

H. Weenen et al. *ACS Symp. Ser.* 1992, 490, 217–231.

E. Jellum et al. *Anal. Chem.* 1973, 45, 1099–1106.

E.E. Kingston et al. *Chem. Abstr.* 1979, 90, 199755m.

M.A. Madson et al. *Carbohydrate Res.* 1981, 94, 183–191.

E. White et al. *Chem. Abstr.* 1983, 98, 103750x.

J.A. Jonckheere et al. *Chem. Abstr.* 1983, 99, 152267z.

D. Gaudry et al. *J. Chromatog.* 1985, 339, 404–409.

F. Stellaard et al. *Clin. Chim. Acta* 1987, 162, 45–51.

O. Pelletier et al. *Clin. Chem.* 1987, 33, 1397–1402.

R.L.M. Dobson et al. *Anal. Chem.* 1990, 62, 1819–1824.

A.D. Parry et al. *Phytochem.* 1990, 29, 1033–1039.

P.E. Haroldsen et al. *J. Lipid Res.* 1991, 32, 723–729.

K.J. Knecht et al. *Arch. Biochem. Biophys.* 1992, 294, 130–137.

J.T. Bemert et al. *J. Chromatog.* 1992, 578, 1–7.

H. Weenen et al. *Chem. Abstr.* 1992, 117, 234348f.

T. Niwa et al. *Biochem. Biophys. Res. Commun.* 1993, 196, 837–843.

*Primary Examiner*—Arlen Soderquist
*Attorney, Agent, or Firm*—Oliff & Berridge

[57] ABSTRACT

For determining 3-deoxyglucosone derivatives which are intermediate metabolites of the Maillard reaction in body fluids such as blood, urine, serum, plasma and the like in gas chromatography/mass spectrometry, $^{13}$C-labelled compounds or $^{14}$C-labelled compounds are useful as an internal standard substance. More specifically, 3-deoxyglucosone derivatives having the formula (I):

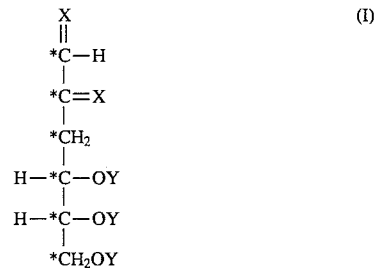

wherein *C is $^{13}$C or $^{14}$C, X is O or N—OR wherein R is Me, Et or H, and Y is SiMe$_3$ or SiMe$_2$tBu, and their production are provided. The measurement of 3-deoxyglucosone derivatives is useful in diagnosing diseases such as diabetes and diseases complicated with diabetes, including diabetic nephrosis, various renal disorders, renal insufficiency, metabolic diseases of carbohydrate and the like.

14 Claims, 5 Drawing Sheets

METHOD FOR MEASURING 3-DEOXYGLUCOSONE DERIVATIVES IN A SAMPLE

This is a division of application No. 08/314,687 filed Sep. 29, 1994.

FIELD OF THE INVENTION

The present invention relates to a method for measuring a sample in mass spectrometry by using a $^{13}$C-labelled compound or a $^{14}$C-labelled compound as an internal standard substance. Specifically, the invention relates to a measuring method based upon a gas chromatography/mass spectrometry using 3-deoxyglucosone derivatives labelled with $^{13}$C or $^{14}$C. The present invention further relates to 3-deoxyglucosone derivatives labelled with $^{13}$C or $^{14}$C, and to a process for producing the same. More specifically, the present invention relates to novel 3-deoxyglucosone derivatives having the formula (I):

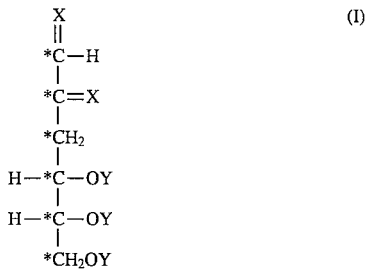

wherein *C is $^{13}$C or $^{14}$C, X is O or N—OR wherein R is Me, Et or H, and Y is SiMe$_3$ or SiMe$_2$tBu and to a process for producing the same. Throughout this specification, Me refers to methyl group, Et refers to ethyl group and tBu refers to tert-butyl group.

BACKGROUND OF THE INVENTION

In recent years, the Maillard reaction between proteins and reducing sugars such as glucose and the like is drawing attention as a cause of degenerating proteins or as a cause of various complications of diabetes.

The Maillard reaction is a reaction in which a mixture of an amino acid or a protein together with a reducing sugar turns into brownish color upon heating. In a first stage, an amino group of a protein or an amino acid reacts with an aldehyde group of a sugar to form a Schiff base compound. A 3-deoxyglucosone derivative is an intermediate metabolite formed as a result of the Maillard reaction and exhibits a strong crosslinking action to proteins.

The crosslinking, polymerization and degeneration of proteins are greatly affected by the Maillard reaction, even for those proteins having particularly long life (crystalline, collagen) suggesting that it is closely related to the aging and degeneration of proteins.

It has therefore been attempted to determine the 3-deoxyglucosone derivatives. In practice, however, there is available no suitable internal standard substance, and correct determination has not been carried out. That is, according to a conventional absolute method, the 3-deoxyglucosone derivative has been directly determined, or a reduced product thereof obtained with NaBD$_4$ has been utilized (e.g., K. Knecht, et al., Archives Biochem Biophy., 294, 130, (1992)).

The 3-deoxyglucosone derivatives are intermediate metabolites of the Maillard reaction and they could not be highly reliably analyzed from body materials and fluids such as blood, urine, hair, skin and tear or from the living body tissues such as various organs, despite attention having been given to such derivatives in regard to aging and various disease conditions such as complications of diabetes.

In recent years, a method has been proposed for determining the 3-deoxyglucosone derivatives owing to the progress in view of the high sensitivity and easy operation in gas chromatography/mass spectrometry which relies on gas chromatography using a mass spectrometer as a detector.

According to the analysis disclosed in Knecht, et al., a 3-deoxyglucosone derivative is reduced with NaBD$_4$ or NaBT$_4$ to form a 3-deoxyhexitol, followed by conversion into an acylated derivative thereof which is subjected to the gas chromatograph mass spectrometer.

According to this analytical method, either a 3-[1,2-$^2$H]-deoxyhexitol or a 3-[1,2-$^3$H]-deoxyhexitol, which is an isotope-labelled compound wherein first and second positions are substituted with deuterium, is used as an internal standard. However, this isotope-labelled compound has a mass number which is larger by only two than a naturally existing one because it is a compound obtained by reducing the 3-deoxyglucosone derivative, and has poor stability in an aqueous solution.

Being added in the stage of preparing samples, the isotope-labelled compound serves as an indication of recovery rate and conversion rate. In order that the determination can be carried out maintaining high precision, it is desired that the isotope-labelled compounds that serve as an internal standard have a different mass number yet also have the same chemical properties as a naturally existing compound and a label at a stable position in the molecules. Therefore, such a substance has been sought.

SUMMARY OF THE INVENTION

The present inventors have sought an internal standard substance for precisely determining a small amount of 3-deoxyglucosone derivative. The inventors have discovered that a 3-deoxyglucosone derivative can be precisely determined by gas chromatography/mass spectrometry (hereinafter simply referred to as GC/MS analysis) when a $^{13}$C$_6$- or a $^{14}$C$_6$-3-deoxyglucosone derivative synthesized from a starting material of a glucose labelled with $^{13}$C or $^{14}$C and a methoxyoxime product thereof are used as an internal standard substance, and have arrived at the present invention.

The present invention relates to novel 3-deoxyglucosone derivatives and to a method of determining the same.

The present invention also relates to a mass spectrometry method utilizing a $^{13}$C- of $^{14}$C-labelled compound as an internal standard substance. Specifically, the present invention relates to a measuring method based on gas chromatography/mass spectrometry.

An amount of 3-deoxyglucosone derivatives is determined by using, as an internal standard substance, a 3-deoxyglucosone derivative which is labelled with $^{13}$C or $^{14}$C and has 1 to 12 more mass numbers per one molecule than naturally occuring compounds. Specifically, the 3-deoxyglucosone derivatives used in the present invention are represented by the general formula (I):

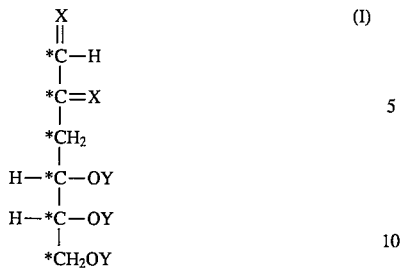

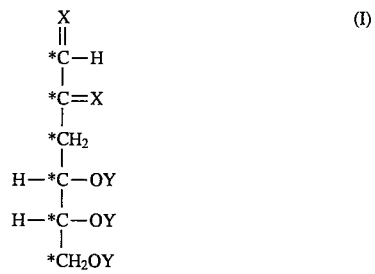

wherein *C is $^{13}$C or $^{14}$C, X is O or N—OR wherein R is Me, Et or H, and Y is SiMe$_3$ or SiMe$_2$tBu.

Samples are pretreated by using a cation exchange resin and an anion exchange resin. Specifically, a $^{13}$C-labelled or $^{14}$C-labelled 3-deoxyglucosone derivative is added to the samples, and the 3-deoxyglucosone derivative is measured by gas chromatography.

As the samples, there can be used, for example, urine, serum, plasma, blood, saliva, body hair, head hair, skin, tear, breath, nail, biopsied living tissues, cell culture solutions, cytoplasmic fluid and organs.

The 3-deoxyglucosone derivatives of the invention are synthesized by using a $^{13}$C- or $^{14}$C-labelled glucose as a starting material. Specifically, the 3-deoxyglucosone derivatives can be prepared by treating a $^{13}$C- or a $^{14}$C-labelled glucose with a hydrazine compound, followed by reacting the obtained hydrazone derivative with an aldehyde compound. The 3-deoxyglucosone derivatives are also prepared through a step of reaction with hydroxylamine or alkoxyamine or a step of silylation.

DETAILED DESCRIPTION OF THE INVENTION

Figure 1:
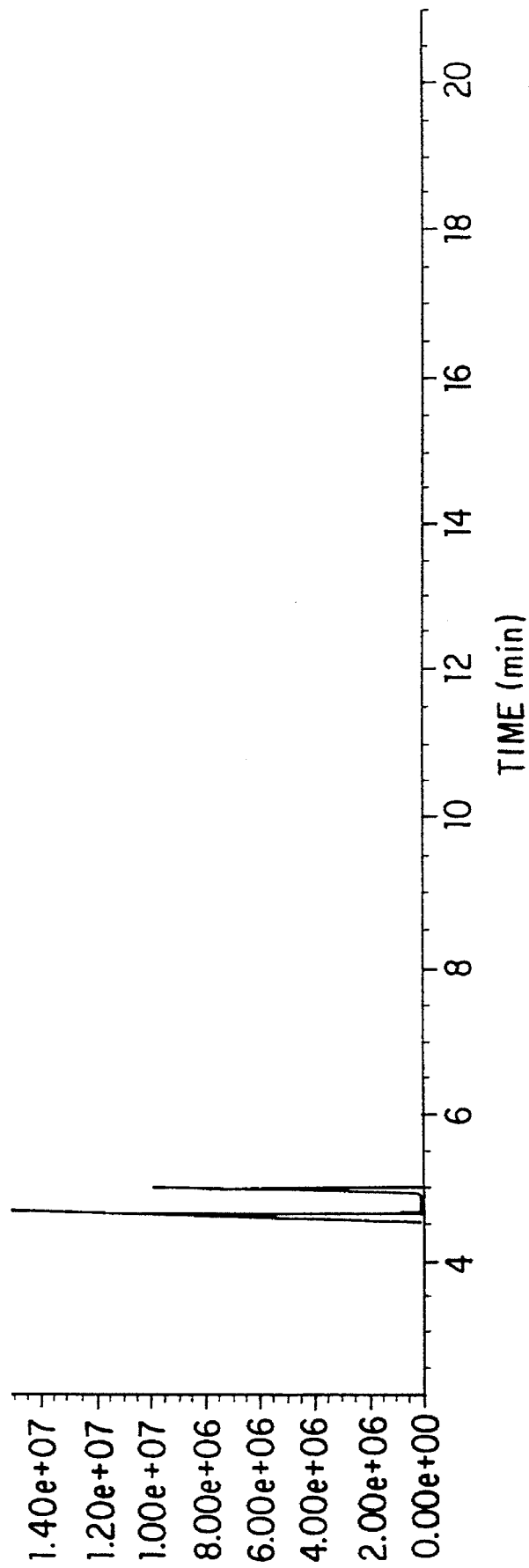
FIG. 1 is a diagram of spectra of a $^{13}$C-3-deoxy-D-erythro-hexose-2-urose 4,5,6-O-trimethylsilyl-1,2-bis-methoxyoxime obtained in Example 3.

The present invention relates to a measuring method which utilizes a $^{13}$C- or $^{14}$C-labelled compound as an internal standard substance, to a $^{13}$C- or $^{14}$C-labelled compound, and to a process for producing the same. Specifically, the invention relates to $^{13}$C-labelled or $^{14}$C-labelled 3-deoxyglucosone derivatives and to a method of measuring the same relying upon a gas chromatography/mass spectrum method. More specifically, the invention relates to 3-deoxyglucosone derivatives represented by the general formula (I):

wherein *C is $^{13}$C or $^{14}$C, X is O or N—OR wherein R is Me, Et or H, and Y is SiMe$_3$ or SiMe$_2$tBu, and to a method of measuring the same.

The 3-deoxyglucosone derivatives are not limited, and include any 3-deoxyglucosone derivative. Compounds of the formulas (III) and (VI) are preferred.

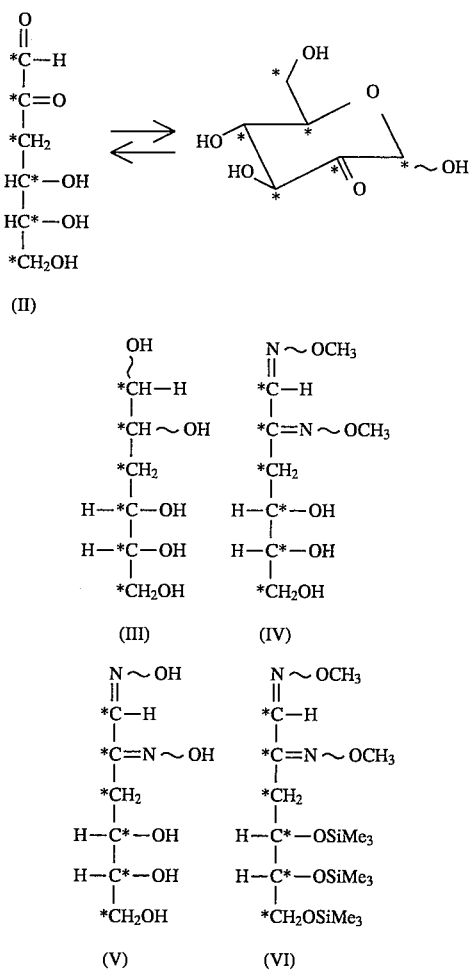

The 3-deoxyglucosone derivatives of the present invention have 1 to 6 $^{13}$C or $^{14}$C per one molecule and have molecular weights which are larger by at least 1 to 12 mass numbers than the naturally existing compounds.

The $^{13}$C$_6$- or the $^{14}$C$_6$-3-deoxyglucosone derivative is obtained by reacting a $^{13}$C- or a $^{14}$C-glucose with a hydrazine compound such as an aromatic hydrazine compound or an aromatic acyl hydrazone compound in the presence of an acid and an aromatic amine, followed by reacting the resulting bishydrazone product with an aldehyde compound such as an aromatic aldehyde compound (transhydrazonation).

Examples of the acid used for the reaction between the glucose and the hydrazine compound include, but are not limited to, inorganic mineral acids such as hydrochloric acid, bromic acid, iodic acid, sulfuric acid, nitric acid, perchloric acid and phosphoric acid, as well as organic acids such as formic acid, acetic acid, propionic acid, tartaric acid, citric acid, p-toluenesulfonic acid and benzoic acid. The reaction solvent in this case can be, for example, water, alcohols such as methanol, ethanol and propanol, ethers such as dimethyl ether, diethyl ether methyl cellosolve, and diisopropyl ether, amides such as dimethylformamide and dimethyl acetamide, as well as dimethyl sulfoxide, acetonitrile, acetone, ethyl methyl ketone, tetrahydrofurane and dioxane.

Examples of the aromatic amine include lower alkyl group-substituted aniline such as p-toluidine, and nitro group- or lower alkoxy group-substituted aniline.

The hydrazine compound can be, for example, an aromatic hydrazine compound or an aromatic acylhydrazone compound. The aromatic hydrazine compound can be a phenyl hydrazine or a phenyl hydrazine wherein the phenyl group may be substituted with a lower alkyl group, a nitro group or a lower alkoxy group. The aromatic acylhydrazone compound can be a benzoylhydrazine or a benzoylhydrazine wherein the phenyl group may be substituted with a lower alkyl group, a nitro group or a lower alkoxy group.

The aldehyde compound can be for example an alicyclic aldehyde compound or an aromatic aldehyde compound. The aromatic aldehyde compound can be a benzylaldehyde, a benzylaldehyde wherein the phenyl group may be substituted by a lower alkyl group, a nitro group or a lower alkoxy group, a benzaldehyde or a benzaldehyde wherein the phenyl group may be substituted by a lower alkyl group, a nitro group or a lower alkoxy group. The alicyclic aldehyde compound can be a cyclohexylaldehyde, a cycloheptylaldehyde, a cyclopentylaldehyde or an alicyclic aldehyde which may be substituted with a lower alkyl group.

More preferably the $^{13}C_6$- or the $^{14}C_6$-3-deoxyglucosone derivative can be obtained by reacting the $^{13}C$- or the $^{14}C$-glucose with a benzoylhydrazone in a solvent such as ethyl alcohol in the presence of p-toluidine and acetic acid, followed by reacting the resulting bis(benzoylhydrazone) product with a benzaldehyde.

The $^{13}C$- or the $^{14}C$-labelled 3-deoxyglucosone represented by the formula (II) can be used in its own form as an internal standard substance but may also be used after it is converted in to a substance which is more stable. Examples of such stabilized substances include 3-deoxyglucosone derivatives represented by the general formula (I), wherein X is N—OR wherein R is an alkyl group or, preferably, a lower alkyl group with 1 to 4 carbon atoms, or H, and Y is H, obtained by treating the $^{13}C$- or $^{14}C$-labelled 3-deoxyglucosone of formula (II) with hydroxylamine or alkoxyamine. More preferably, there can be exemplified $^{13}C$- or $^{14}C$-labelled 3-deoxyglucosone derivatives represented by the formula (IV) obtained by treating the $^{13}C$- or $^{14}C$-labelled 3-deoxyglycosone represented by the general formula (II) with methoxyamine hydrochloride.

The hydroxylamine or the alkoxylamine is used in the form of a hydrochloride thereof. As the alkoxylamine, there can be used a methoxylamine, an ethoxylamine, a propyloxylamine, an isopropyloxylamine, a butoxylamine or an isobutoxylamine. Among them, it is preferable to use methoxylamine and ethoxylamine.

There can be further exemplified $^{13}C$- or $^{14}C$-labelled 3-deoxyglucosone derivatives represented by the formula (VI) obtained by treating the 3-deoxyglucosone derivative represented by the general formula (I) wherein X is O or N—OR wherein R is an alkyl group and, preferably, a lower alkyl group with 1 to 4 carbon atoms, or H and Y is H with a silylating agent to introduce silyl groups into the free hydroxyl groups.

The silylating agent can be suitably selected from those that are known in this field of art. For example, there can be used a trimethyl silylating agent, a dimethyl silylating agent or a halomethyl silylating agent. Examples of the trimethyl silylating agent include a hexamethyldisilazane, trimethylchlorosilane, N,O-bis(trimethylsilyl)acetamide, N-trimethylsilyl diethylamine, N-trimethylsilyl dimethylamine, N-methyl-N-trimethylsilyl acetamide, N-methyl-N-trimethylsilyl trifluoroacetamide, N-trimethylsilyl imidazole and the like. Examples of the dimethyl silylating agent include t-butyldimethylsilylimidazole, N,O-bis(diethylhydrogensilyl)trifluoroacetamide, t-butyldimethylchlorosilane, dimethylethylchlorosilane, dimethyl-n-propylchlorosilane, dimethylisopropylchlorosilane, dimethylchlorosilane, tetramethyldisilazane and the like. Examples of the halomethyl silylating agent include bromomethyldimethylchlorosilane, chloromethyldimethylchlorosilane and the like.

The silylating agent can be suitably selected from those that are commercially available. Examples include a hexamethyldisilazane-trimethylchlorosilane-pyridine such as TMS-HT (trade name, Tokyo Kasei Kogyo Co., Japan) and Sylon-HTP (trade name, Spelco Japan Co., Japan), an N,O-bis(trimethylsilyl)acetamide-acetonitrile such as TMS-BA (trade name, Tokyo Kasei Kogyo Co., Japan), an N,O-bis(trimethylsilyl)trifluoroacetamide-trimethylchlorosilane and an N,O-bis(trimethylsilyl)acetamide-trimethylchlorosilane such as Sylon-BFT (trade name, Spelco Japan Co., Japan) and Sylon-BT (trade name, Spelco Japan Co., Japan), an N,O-bis(trimethylsilyl)acetamide-trimethylchlorosilane-N-trimethylsilylimidazole such as Sylon-BTZ (trade name, Spelco Japan Co., Japan), an N-trimethylsilylimidazolepyridine such as Sylon-TP (trade name, Spelco Japan Co., Japan), and TMS-PZ (trade name, Tokyo Kasei Kogyo Co., Japan).

Further examples of suitable compounds include those obtained by treating 3-deoxyglucosone derivatives represented by the general formula (I) wherein x is O, N—OR wherein R is an alkyl group and, preferably, a lower alkyl group with 1 to 4 carbon atoms, or H, and Y is H with a trifluoroacetylating agent to introduce trifluoroacetylating groups to the free hydroxyl groups.

Gas chromatography is a process known in the art, as is the apparatus, and its component parts, for carrying out gas chromatography. In gas chromatography, there is used a metallic column such as of stainless steel, copper or aluminum, or a glass column such as of Pyrex glass treated with silane. The column used in the gas chromatography can be suitably selected from those known in this field of art or from those commercially available. As the stationary phase of the packed column, there can be used an adsorbent of the type of porous polymer such as a porous polystyrene divinylbenzene polymer or a porous diphenyl phenylene oxide polymer, or an adsorbent such as spherical porous silica, alumina, activated carbon, Molecular Sieves or silica gel.

As the liquid stationary phase, furthermore, there can be used methyl silicone, phenyl silicone, trifuloropropyl silicone, cyanoethylmethyl silicone, neopentyl glycol adipate, neopentyl glycol succinate, polyethylene glycol, ethylene glycol adipate, butanediol succinate, diethylene glycol adipate, diethylene glycol succinate, cyanopropylmethyl silicone, ethylene glycol succinate, alkylene glycol phthalic acid ester, and the like. As a carrier for the liquid phase, there can be used a carrier obtained by treating diatomaceous earth with alkali, acid, silane or heat. There can be further used a Teflon carrier, a terephthalic acid carrier, a fluorine-containing resin carrier, a quartz carrier, a porous polymer carrier or a glass carrier. If necessary, the above carriers can be treated with silane by using the aforementioned silylating agents.

As the capillary column, there can be used a molten silica capillary column coated with a heat resistant polyimide resin or aluminum. The capillary column can be suitably selected from those known in this field of art or from those commercially available.

The sample isolated by the gas chromatography is preferably subjected to detection and measurement through mass spectrometry. Moreover, the sample isolated by the gas chromatography preferably is subjected to detection and measurement through the plasma chromatography.

The isolated molecules can be ionized by, for example, an electron bombardment ionization, a chemical ionization, an electric field ionization or the like.

As a general analytical method, the compound (II) or (III), for example, is added in a predetermined amount to a sample that is to be determined, and the sample is subjected to gas chromatography.

Examples of the sample include body fluids such as urine, serum, blood, tear, breath and saliva, living body tissues such as body hair, head hair, skin, nail, biopsied living tissue, cell culture solutions, cytoplasmic fluid, organs, as well as cultured products thereof, which are considered to contain 3-deoxyglucosone or derivatives thereof.

The sample can be subjected to ion exchange chromatography. The ion exchange chromatography may be a cation exchange chromatography, an anion exchange chromatography, or a combination thereof. An ion exchange filler used therefor may be a porous polymer such as styrene-divinyl benzene copolymer, or a porous silica such as cellulose or crosslinked cellulose to which is introduced a sulfonic acid group, a carboxyl group or a quaternary amine group. Representative examples of the group to be introduced are a diethylaminoethyl group and a quaternary amine group in the case of the anion exchange, and a carboxymethyl group and a sulfopropyl group in the case of the cation exchange. The ion exchange filler can be suitably selected from those that have been known in this field of art or from those that are commercially available.

The 3-deoxyglucosone or derivatives thereof are intermediate metabolites of the Maillard reaction. Attention has been given to their relationship to aging and various diseases such as complications of diabetes. By precisely determining the 3-deoxyglucosone or derivatives thereof as contemplated by the present invention, it becomes possible to diagnose such diseases. In particular, precise determination and analysis of trace amounts thereof are helpful for diagnosing complications of diabetes such as diabetic nephrosis, renal insufficiency, metabolic diseases of carbohydrate, as well as for diagnosing aging and degeneration of proteins.

In measuring 3-deoxyglucosone derivatives in a sample from a living body, a gas chromatographic mass spectrometry using a $^{13}$C- or $^{14}$C-labelled 3-deoxyglucosone derivative as an internal standard substance makes it possible to accurately find the content of the 3-deoxyglucosone derivatives in the sample.

Accordingly, by precisely determining and analyzing a small amount of 3-deoxyglucosone derivatives in a living body sample such as body fluid, e.g., urine, serum, blood, plasma, tear, breath or saliva, or a living body tissue, e.g., body hair, head hair, skin, nail, biopsied living tissue, cell culture solution, cytoplasmic fluid or organs, or a cultured product thereof, it becomes possible to diagnose diabetes and complications of diabetes such as diabetic nephrosis, renal insufficiency, metabolic diseases of carbohydrate and to diagnose aging and degeneration of proteins.

EXAMPLES

The invention will now be illustrated by examples. The examples are not intended to be limiting of the scope of the present invention. In conjunction with the description above, the examples bis provide further understanding of the present invention.

Example 1

Synthesis of a $^{13}$C-3-deoxy-D-erythro-hexose-2-urose bis (benzoylhydrazone). In the reaction diagram below, Bz represents benzoyl.

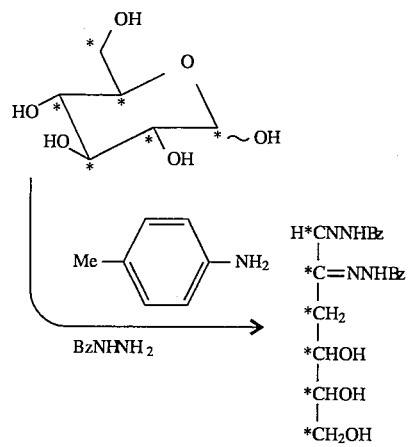

A $^{13}$C-glucose (2.0 g, 10.7 mmol, 1.0 eq.) produced by Shoko Tsusho Co., Japan and a p-toluidine (1.1 g, 10.3 mmol, 0.92 eq.) are suspended in 95% ethyl alcohol (45 ml) and acetic acid (2.2 ml), and are heated and stirred at 120° C. for 30 minutes under argon stream. The reaction solution becomes homogeneous after 5 minutes and exhibits a brownish color after 30 minutes. To this solution is added a benzoyl hydrazone (3.3 g, 24.4 mmol, 2.18 eq.), followed by heating and refluxing for 7 hours under an argon atmosphere. Crystals precipitate after the reaction solution of the brownish color is left to stand overnight at 4° C.

The crystals are separated by using a glass filter and are readily washed with cold methyl alcohol (20 ml×3) and then with cold diethyl ether (20 ml×3). The washing solution is air-dried at room temperature to obtain crude crystals of a $^{13}$C-3-DG-bis-benzoyl hydrazone (1.6 g, 36.8%). The crude crystals are recrystallized from 95% ethyl alcohol (100 ml) to obtain white needle-like crystals (1.25 g, 28.7%) having the following propeties:

Melting point: 174°–175° C.

$[\alpha]D^{25}$: 10.2 (c0.6 pyridine)

Mass spectrum (m/e): 386 (M-18)

Elemental analysis (%):

Found: C, 56.9; H, 5.6; N, 13.3,

Calculated for $C_{20}H_{22}N_4O_6/H_2O$: C, 56.9; H, 5.73; N, 13.26

$^1$H-NMR($\delta$ ppm, DMSO-$d_6$):

12.93 (br, 1H, NH, extinguished upon the addition of deuterium), 12.09 (br, 1H, NH, extinguished upon the addition of deuterium), 8.36 (s, 0.5H, CH)), 8.02 (s, 0.5H, CHO), 7.9 (m, 4H, aromatic ring), 7.5 (m, 6H, aromatic ring), 6.15 (br, 1H, OH, extinguished upon the addition of deuterium), 5.04 (br, 1H, OH, extinguished upon the addition of deuterium), 4.52 (br, 1H, OH, extinguished upon the addition of deuterium), 3.99 (s, 0.5H), 3.71 (s, 1H), 3.55 (s, 1H), 3.43 (m, 0.5H), 3.30 (s, $H_2O$), 3.28 (m, 1.5H), 3.02 (br, 1H), 2.78 (br, 0.5H), $^{13}C$-NMR(DMSO-$d_6$):

28.26(t), 62.53(d), 70.95(t), 74.39(t), 148.25(d), 154.5(m)

Similarly, by using the procedures described herein and $^{14}C$-glucose, $^{14}C$-3-DG-bis-benzoyl hydrazone is prepared.

Example 2

Synthesis of a $^{13}C$-3-deoxy-D-erythro-hexose-2-urose (3DG).

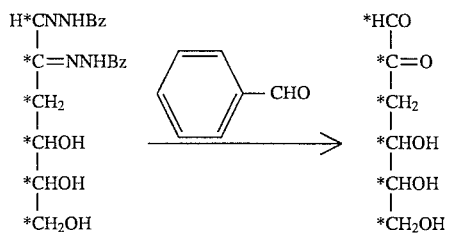

A mixture solution of a $^{13}C$-3-DG-bis benzoyl hydrazone (808.8 mg, 2.0 ml, 1.0 eq.), ethyl alcohol (24 ml), acetic acid (0.5 ml), distilled water (40 ml) and fresh distilled (30 mmHg, 82° C.) benzaldehyde (1.3 ml, 12.5 mmol, 6.2 eq.) is introduced into a 100-ml eggplant type flask, and is heated and refluxed under argon atmosphere for 4 hours. After 15 minutes pass, the reaction solution becomes homogeneous, colorless and transparent. After the reaction, 40 ml of distilled water is added to the reaction solution of pale yellow color, resulting in the formation of white precipitate. In this state, 24 ml of the solvent is distilled off from the reaction solution under ambient pressure. The suspension is left to stand overnight at 4° C., and the precipitate is separated by using a glass filter No. 3. The precipitate is a benzaldehyde benzoylhydrazone (δ 18.5 mg, recovery of 91.2%). The precipitate is washed with distilled water (10 ml×3) and is neutralized with an ion exchange resin IRA-410(OH)(2.28 g). The filtrate is concentrated into 20 ml under a reduced pressure (37° C., 12 mmHg) using a rotary evaporator. The solution is extracted with diethyl ether (10 ml×8) to remove yellow components. Ether in the water layer is slightly heated (40° C.) and removed, and the solution is filtered after the treatment with activated carbon (200 mg). The filtering paper is washed with distilled water (5 ml×3). The water layer (45 ml) is concentrated into 1.41 ml under a reduced pressure (12 mmHg). When 20 ml of hot (60° C.) ethyl alcohol is added, precipitate is formed after 30 minutes to 6 hours. The precipitate is filtered and the filtrate is concentrated under a reduced pressure to obtain a pale yellowish product (387.9 mg). The product is dissolved in 20 ml of distilled water, to which is added a mixture of ion exchange resins, Amberlites IR-120B(H) (1.5 g) and IRA-410 (OH)(1.5 g), followed by stirring and decantation to obtain a pale yellowish solution which is then concentrated and dried to obtain a crude product (248.8 mg). The product is purified by using a silica gel chromatography (φ2.5×9.5 cm, 14.4 g). By using dichloromethane:methyl alcohol:distilled water=100:10:1, there are obtained fractions Fr. 10–15 (54.5 mg), Fr. 16–25 (71.9 mg) and Fr. 26–35 (33.7 mg). The three fractions are subjected together again to the chromatography (φ2.5×11 cm, 16 g, φ2.5×10 cm, 15 g) two times. By using chloroform:methyl alcohol:distilled water= 100:10:1, fractions Fr. 13-18 (41.6 mg), Fr. 19-22 (35.5 mg) and Ft. 23-28 (25.4 mg) are obtained.

Each fraction is dissolved in 2 ml of distilled water and is freeze-dried to afford a white amorphous powder.

Mass spectrum (m/e): 138 (M-30)

Thin layer chromatography: Rf=0.48 chloroform:methyl alcohol:distilled water (7:3:0.5)

IR (cm$^{-1}$): 3400W, 1640S

Similarly, by using the procedures described herein and $^{14}C$-3-DG-bis-benzoyl hydrazone, $^{14}C$-3-deoxy-D-erythrol-hexose-2-urose is prepared.

Example 3

Synthesis of a $^{13}C$-3-deoxy-D-erythro-hexose-2-urosebismethoxyoxime.

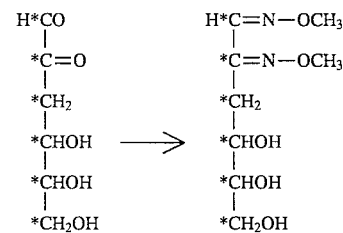

A $^{13}C$-3-deoxy-D-erythro-hexose-2-urose (35.5 mg, 0.211 mmol, 1.0 eq.), a methoxamine hydrochloride (39.5 mg, 0.464 mmol, 2,2 eq.) and pyridine (1.0 ml) are introduced into a 25-ml eggplant type flask, and are stirred at room temperature for 7 hours. The reaction is complete in three hours. The solvent is distilled off from the reaction liquid under a reduced pressure, and the residue is isolated and purified through a silica gel chromatography (φ2.5×6.7 cm, 10 g). When the effluent is ethyl acetate, there is obtained $^{13}C$-3-deoxy-D-erythro-hexose-2-urose-bismethoxyoxime as a colorless oil (28.2 mg, 58.9%).

Colorless oil

Thin layer chromatography: R=0.33 ethyl acetate

Mass spectrum (M/e): 195 (M-31), 180 (M-31-15), 163 (M-31-15-17).

Similarly, by using the procedures described herein and $^{14}C$-3-deoxy-D-erythro-hexose-2-urose, $^{14}C$-3-deoxy-D-erythro-hexose-2-urose-bismethoxyoxime is prepared.

Example 4

Figure 2:
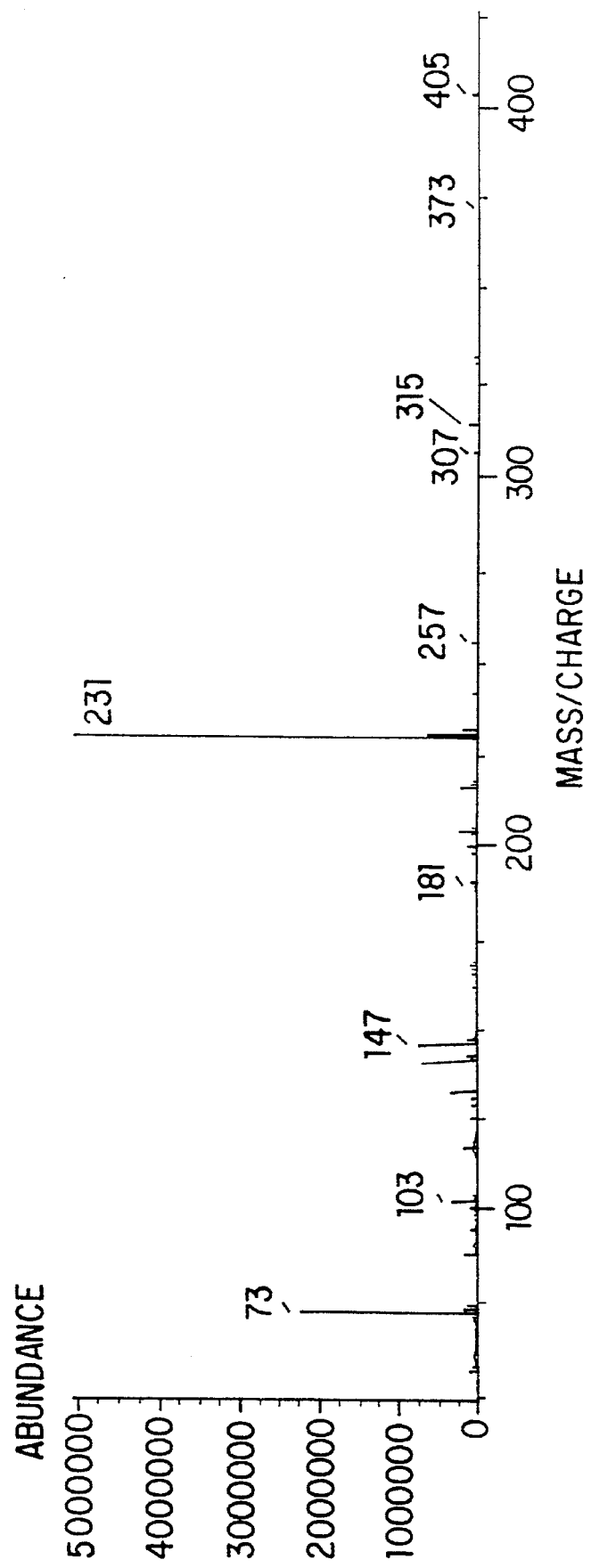
FIG. 2 is a diagram of spectra of a $^{12}$C-3-deoxy-D-erythro-hexose-2-urose 4,5,6-O-trimethylsilyl-1,2-bis-methoxyoxime.
Figure 3:
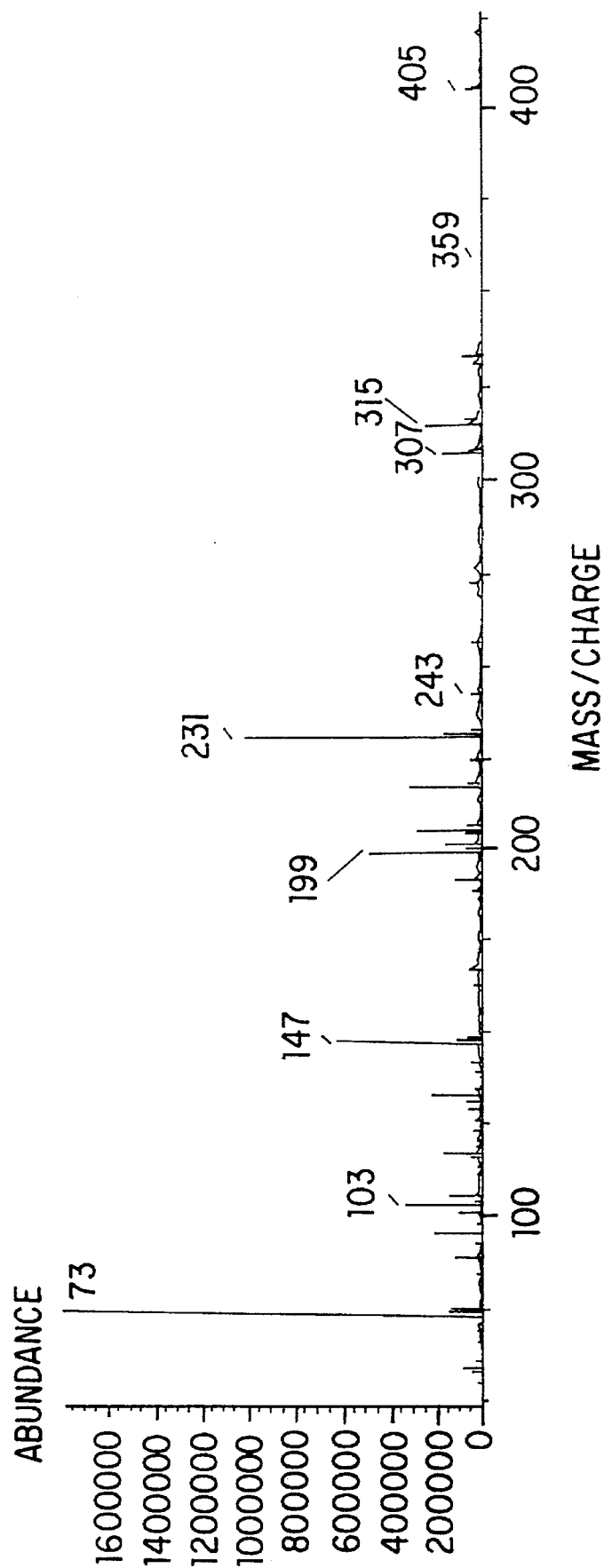
FIG. 3 is a diagram of spectra of a $^{12}$C-3-deoxy-D-erythro-hexose-2-urose 4,5,6-O-trimethylsilyl-1,2-bis-methoxyoxime.
Figure 4:
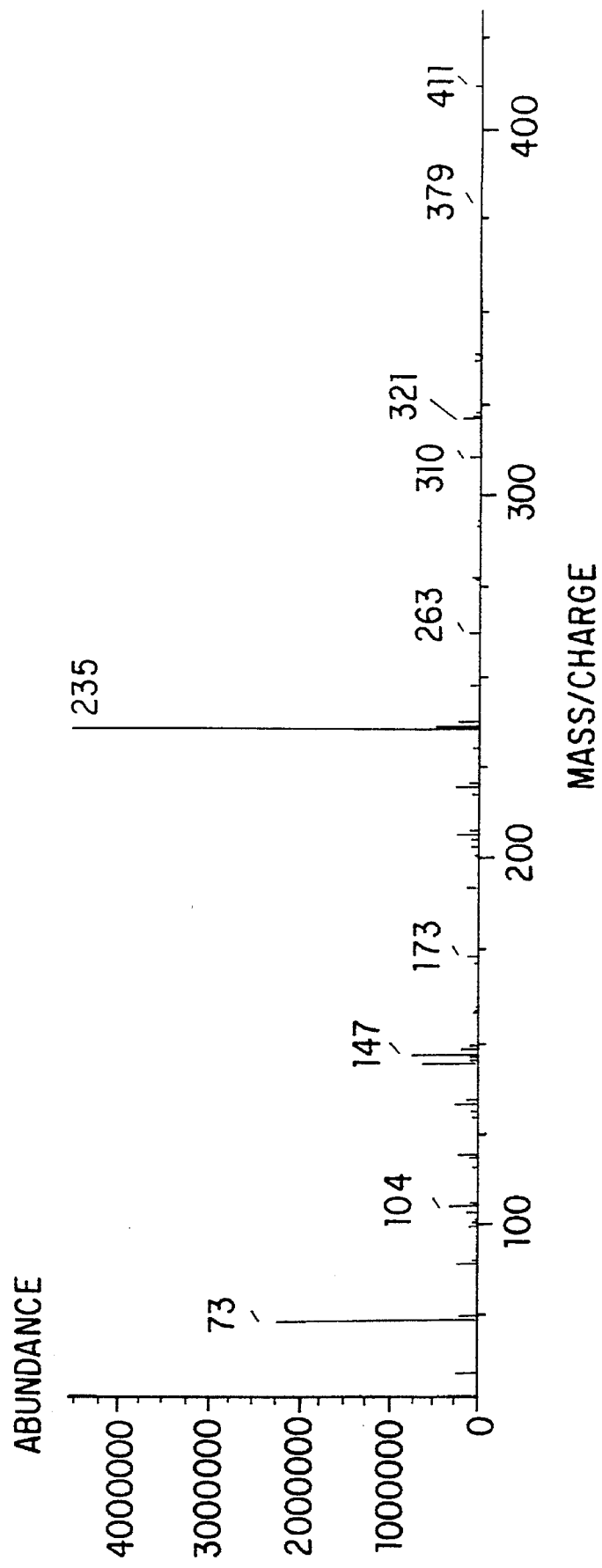
FIG. 4 is a diagram of spectra of a $^{13}$C-3-deoxy-D-erythro-hexose-2-urose 4,5,6-O-trimethylsilyl-1,2-bis-methoxyoxime.
Figure 5:
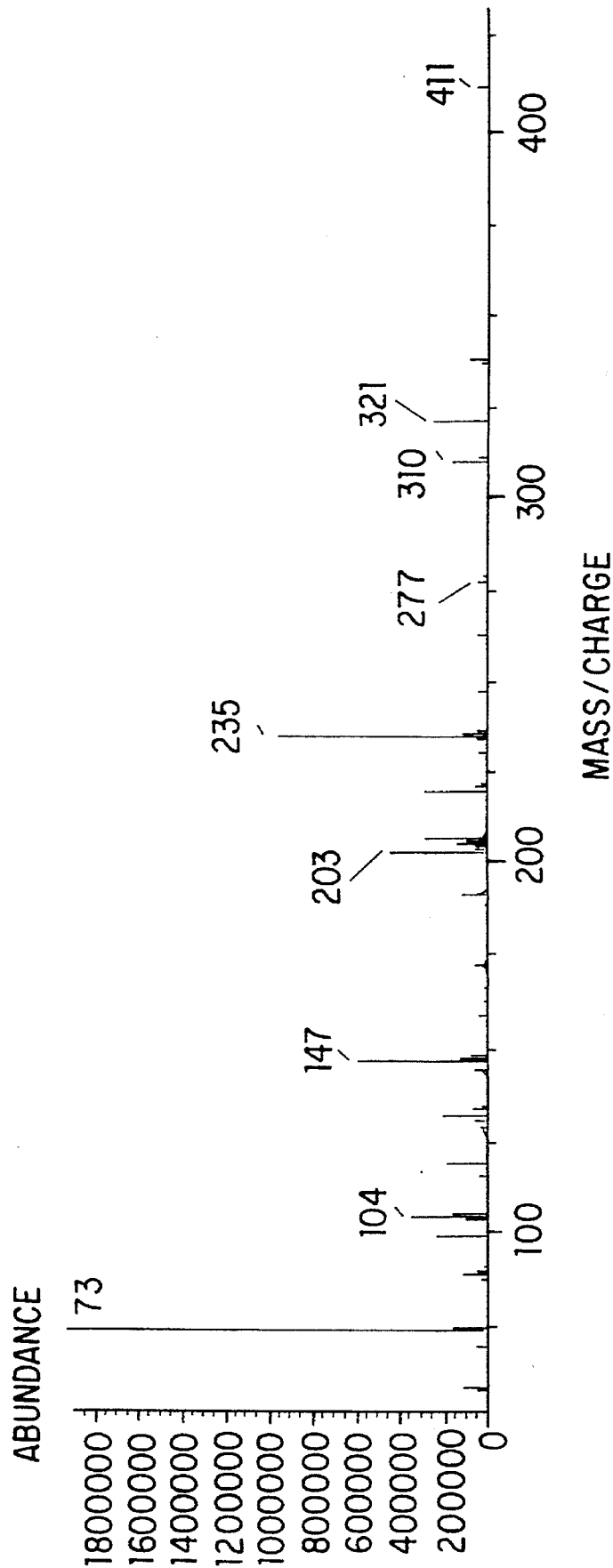
FIG. 5 is a diagram of spectra of a $^{13}$C-3-deoxy-D-erythro-hexose-2-urose 4,5,6-O-trimethylsilyl-1,2-bis-methoxyoxime.

To 10 μg of the C-3-deoxy-D-erythro-hexose-2-urose-bismethoxyoxime obtained in Example 3 is added 20 ml of an N,O-bis(trimethylsilyl) trifluoroacetamide containing 1% of trimethylchlorosilane to react them at 60° C. for 20 minutes. After this trimethylsilylation, the product $^{13}C$-3-deoxy-D-erythro-hexose-2-urose 4,5,6-O-trimethylsilyl-1,2-bismethoxyoxime is analyzed by using a gas chromatography/mass spectrometer, Model HP5890+HP5970B manufactured by Hewlett-Packard Co. by holding the product at 150° C. for one minute, raising the temperature at a rate of 10° C. per minute, and holding the product at 310° C. for 3.5 minutes. As shown in FIG. 4, the product exhibits a characteristic peak at m/e 235 which is larger by 4 mass numbers than the $^{12}C$-3-deoxy-D-erythro-hexose-2-urose 4,5,6-O-trimethylsilyl 1,2-bismethoxyoxime shown in FIG. 2, and the product is identified with $^{13}$C-3-deoxy-D-erythro-hexose-2-urose 4,5,6-O-trimethylsilyl 1,2-bismethoxyoxime. It is further found owing to CI-SIM that the conventional compound exhibits a peak at 437 while the compound of the present invention exhibits a peak at 443. It is thus made possible to determine the 3-deoxyglucosone derivatives by using the internal standard method.

Similarly, by using the procedures described herein and $^{14}$C-3-deoxy-D-erythro-hexose-2-urose-bismethoxyoxime, $^{14}$C-3-deoxy-D-erythro-hexose-2-urose 4,5,6-O-trimethylsilyl 1,2-bismethoxyoxime is prepared and it is possible to determine the 3-deoxyglucosone derivatives by using the internal standard method.

Example 5

Preparation of sample: 200 ng of the $^{13}$C-3-deoxy-D-erythro-hexose-2-urose which is a $^{13}$C$_6$-3-deoxyglucosone derivative prepared according to the present invention as an internal standard substance is added to 1 ml of serum from a normal healthy person (or serum from a patient suffering from diabetes or serum from a patient suffering from stomach disease). The sample is then sufficiently mixed with a 0.05 M phosphoric acid buffer solution (pH 7.0) containing glucose oxidase (100 µ/ml), catalase (1100 µ/ml) and mutarotase (4 µ/ml), and is incubated at 37° C. for one hour. After addition of 2 ml of ethyl alcohol to the solution, the mixture is subjected to centrifuge at 3000 rpm for 10 minutes to remove denatured proteins. The supernatant liquid is added to Bond Elut SCX cartridge (cation exchange resin 100 mg/ml, Analytichem International Inc., Harbor City, Calif., USA) and is eluted with 3 ml of distilled water. The collected eluate is added to Bond Elut SAX cartridge (anion exchange resin 100 mg/ml, Analytichem International) and is eluted with 3 ml of distilled water. The eluate is collected and is freezedried. The eluate is dissolved in methyl alcohol, transferred into a vial with a screw cap, and the solvent is removed under nitrogen stream. Then, to 200 µl of pyridine is added a solution containing 5 mg of methoxylamine hydrochloride to carry out the reaction at 70° C. for 30 minutes to form a methoxyoxime derivative. After the solvent is removed under nitrogen stream, 20 µl of N,O-bis(trimethylsilyl) trifluoroacetamide containing of triethylamine is added thereto to carry out the reaction at 60° C. for 20 minutes to convert the hydroxyl group into a trimethylsilyl derivative. After left to cool, 5 µl of the sample is analyzed through gas chromatography/mass spectrometry (GC/MS). When serum from a normal person is used, the deviation coefficients among the samples and in the samples are as small as 7% (n=5) and 6.3% (n=5) up to the concentration of 800 ng/ml. The recovery rate of the 3-deoxyglucosone derivative that is added is nearly 100.0% wherein its standard deviation is 4.6% (average value±standard deviation n=5).

Example 6

GC/MS: A portable needle-type instrument with an injector equipped with a capillary column, DB-17 (30 m×0.32 mm, 15 µm in inner diameter, J & W Scilntibic, Folsom, Calif., USA) in which 50% phenylmethyl silicon is coupled to a gas chromatography, GC-9A, produced by Shimazu Co., Japan equipped with a double convergence-type mass spectrometer.

The column temperature is raised from 140° C. to 200° C. at a rate of 5° C./min. The injector temperature is 280° C., the separator temperature is 280° C., the ion source temperature is 250° C., and the EI mass spectrum is measured at an ionization voltage of 70 eV. The uptake current is 60 µA and the acceleration voltage is 3 KV. The CI mass spectrum is carried out by using isobutane as a reaction gas and an ionization voltage of 150 eV. SIM (selected ion monitoring) is used for determining the $^{13}$C-3-deoxy-D-erythro-hexose-2-urose 4,5,6,O-trimethylsilyl-1,2-bismethoxyoxime.

Example 7

Results of sample measurement:

Serums are corrected from a standard serum mixture, normal person and a patient suffering from diabetes, and are measured for their EI-SIM and CI-SIM. Since CI-SIM from which the result (molecular ions +H) appears exhibits peaks at 437 and 443, the 3-deoxyglucosone derivatives in the serums are determined by using these values. The conditions for measuring GC/MS are as described in Example 5.

When ions are monitored with SIM, the sample exhibits a peak at 437 and the internal standard product (substance of the present invention) that is added exhibits a peak at 443. As fragments, the sample exhibited a peak at 231 and the internal standard substance exhibits a peak at 235.

Therefore, the amount of 3DG in the sample can be precisely determined from the calibration curve (method of Example 5) that has been prepared in advance. When there is no internal standard substance, only the peak 437 or 231 can be observed, making it difficult to accomplish the determination.

437 and 443 are different by a mass number of 6, and can serve as exact internal standard substances.

The sample prepared according to the method of Example 5 is measured for the $^{13}$C-3-deoxy-D-erythro-hexose-2-urose which is the 3-deoxyglucosone, and the following results are obtained.

|  | Number of samples | Measured according to the present invention |
| --- | --- | --- |
| Normal healthy person | 18 | 314 ± 28 |
| Diabetes | 30 | 778 ± 148 |
| Kidney disease | 27 | 1476 ± 202 | average value ± standard error

There is used a $^{14}$C-3-deoxy-D-erythro-hexose-2-urose 4,5,6,O-trimethylsilyl-1,2-bismethoxyoxime that is a $^{14}$C$_6$-3-deoxyglucosone derivative synthesized in the same manner by using the $^{14}$C-glucose.

The same results are obtained through the measurement.

As described above, the invention of the present application not only makes it possible to easily measure the 3-deoxyglucosone derivatives but also teaches that the concentration of 3-deoxyglucosone derivatives in the serum changes reflecting the disease. By measuring the 3-deoxyglucosone derivatives in the serum, on the other hand, it becomes possible to diagnose diseases such as diabetes and diseases complicated with diabetes, including diabetic nephrosis, various renal disorders, renal insufficiency, metabolic diseases of carbohydrate and the like.

In contrast with the prior art in which labelled molecules are unstable in an aqueous solution, the method of the present invention offers measured results with improved reliability, which is an excellent measuring method.

As apparent from the foregoing description, the present invention makes it possible to determine the 3-deoxyglucosone derivatives in living body samples while maintaining high sensitivity.

What is claimed is:

1. A method for measuring an analyte in a sample to be determined, which comprises analyzing the sample in a mass spectrometer by utilizing a $^{13}$C- or $^{14}$C-labelled 3-deoxyglucosone derivative as an internal standard substance, wherein the 3-deoxyglucosone derivative is a compound having the formula (I):

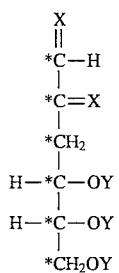

wherein *C is $^{13}$C or $^{14}$C, X is O or N—OR wherein R is Me, Et or H, and Y is SiMe$_3$ or SiMe$_2$tBu.

2. A method according to claim 1, wherein the mass spectrometer is a gas chromatography/mass spectrometer.

3. A method according to claim 1, wherein the 3-deoxyglucosone derivative is a compound having the formula (VI):

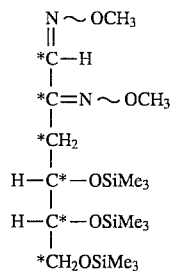

wherein *C is $^{13}$C or $^{14}$C.

4. A method according to claim 1, wherein the sample is prepared through pretreatment with a cation exchange resin and an anion exchange resin.

5. A method according to claim 1, wherein said $^{13}$C- or $^{14}$C-labelled 3-deoxyglucosone derivative is added to the sample, and the 3-deoxyglucosone derivative is measured by gas chromatography method.

6. A method according to claim 1, wherein the sample is a living body tissue.

7. A method according to claim 6, wherein the living body tissue is selected from the group consisting of urine, serum, blood, saliva, body hair, head hair, skin, tear, breath, nail, biopsied living tissue, cell culture solutions, cytoplasmic fluid and organs.

8. A method according to claim 1, wherein the measurement is for diagnosing diabetes, diseases complicated with diabetes, aging or degeneration of proteins.

9. A method according to claim 8, wherein the diseases complicated with diabetes are diabetic nephrosis, renal insufficiency, or metabolic diseases of carbohydrates wherein when said disease complicated with diabetes is said metabolic disease of carbohydrate, said analyte is 3-deoxyglucosone and the measurement is for a serum level of said 3-deoxyglucosone being less than 286 ng/ml or greater than 342 ng/ml.

10. A method according to claim 9, wherein the disease is said metabolic disease of carbohydrate, said analyte is 3-deoxyglucosone, and the measurement is for a serum level of said 3-deoxyglucosone being less than 286 ng/ml or greater than 342 ng/ml.

11. A method according to claim 1, further comprising determining an amount of the analyte in the sample by comparing the sample to a standard reference not including said analyte.

12. A method according to claim 1, wherein the sample is prepared by a process comprising the steps of:
  (a) adding said 3-deoxyglucosone derivative to said sample to form a sample solution;
  (b) adding a buffer solution to said sample solution of step (a);
  (c) centrifuging said sample solution to remove denatured proteins and produce a supernatant liquid;
  (d) subjecting said supernatant liquid to cation exchange processing and anion exchange processing to form a second sample solution; and
  (e) forming a methoxyoxime derivative of said second sample solution and silylating said second sample solution.

13. A method according to claim 12, wherein the buffer solution comprises glucose oxidase and mutarotase.

14. A method for measuring an analyte of a 3-deoxyglucosone derivative in a sample to be determined, which comprises analyzing the sample in a mass spectrometer by utilizing a $^{13}$C- or $^{14}$C-labelled compound as an internal standard substance, wherein the $^{13}$C- or $^{14}$C-labelled compound is a compound having the formula (I):

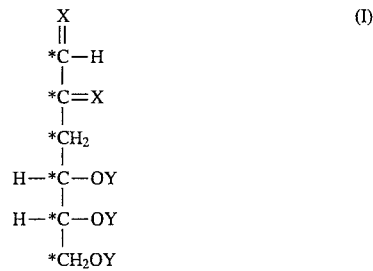

wherein *C is $^{13}$C or $^{14}$C, X is O or N—OR wherein R is Me, Et or H, and Y is SiMe$_3$ or SiMe$_2$tBu.

* * * * *